(12) United States Patent
Schabbach et al.

(10) Patent No.: US 8,864,740 B2
(45) Date of Patent: Oct. 21, 2014

(54) NEEDLE ASSEMBLY WITH RELEASE MECHANISM

(75) Inventors: Michael Schabbach, Frankfurt am Main (DE); Daniel Wagner, Frankfurt am Main (DE); Houda Mihad, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/825,840

(22) PCT Filed: Sep. 28, 2011

(86) PCT No.: PCT/EP2011/066800
§ 371 (c)(1),
(2), (4) Date: Mar. 25, 2013

(87) PCT Pub. No.: WO2012/041870
PCT Pub. Date: Apr. 5, 2012

(65) Prior Publication Data
US 2013/0197477 A1 Aug. 1, 2013

Related U.S. Application Data

(60) Provisional application No. 61/388,644, filed on Oct. 1, 2010.

(30) Foreign Application Priority Data

Nov. 11, 2010 (EP) .................................... 10190793

(51) Int. Cl.
*A61M 31/00* (2006.01)
*A61M 5/28* (2006.01)
*A61M 5/32* (2006.01)
*A61M 5/178* (2006.01)

(52) U.S. Cl.
CPC ....... *A61M 5/329* (2013.01); *A61M 2005/1787* (2013.01); *A61M 5/284* (2013.01); *A61M 5/3294* (2013.01)
USPC ............ 604/506; 604/192; 604/201; 604/241

(58) Field of Classification Search
CPC ................ A61M 5/284; A61M 5/329; A61M 2005/1787
USPC .......... 604/192, 200–203, 206, 240–244, 506
See application file for complete search history.

(56) References Cited

U.S. PATENT DOCUMENTS 2,554,451 A 5/1951 Barry
(Continued)

FOREIGN PATENT DOCUMENTS

WO 88/02265 4/1988
WO 2010/139671 12/2010

OTHER PUBLICATIONS

International Preliminary Report on Patentability for Int. App. No. PCT/EP2011/066800, mailed Apr. 11, 2013.
(Continued)

*Primary Examiner* — Theodore Stigell
(74) *Attorney, Agent, or Firm* — McDonnell Boehnen Hulbert & Berghoff LLP

(57) ABSTRACT

A needle assembly comprises a body configured for attachment to a drug delivery device. The body defines a cavity. A septum is positioned within the cavity and a stopper positioned within the cavity such that the cavity, septum, and stopper define a reservoir. A double ended needle is positioned in the stopper and septum, the needle comprising a proximal end and a distal end. A release mechanism is positioned near a distal end of the body. A biasing element is positioned to drive the stopper. During a dose dispensing step, the release mechanism drives the proximal end of the needle out of the septum so that the proximal end resides in said reservoir. The biasing element may also drive the stopper proximally.

14 Claims, 5 Drawing Sheets

(56) References Cited

U.S. PATENT DOCUMENTS

| | | | |
|---|---|---|---|
| 4,394,863 A | 7/1983 | Bartner | |
| 5,086,783 A * | 2/1992 | Macors et al. | 600/578 |
| 8,241,257 B2 * | 8/2012 | Wei | 604/242 |
| 2004/0138611 A1 | 7/2004 | Griffiths et al. | |
| 2006/0276755 A1 | 12/2006 | Sullivan et al. | |
| 2012/0041379 A1 * | 2/2012 | Macarthur et al. | 604/192 |

OTHER PUBLICATIONS

International Search Report and Written Opinion for Int. App. No. PCT/EP2011/066800, completed Jan. 18, 2012.

* cited by examiner

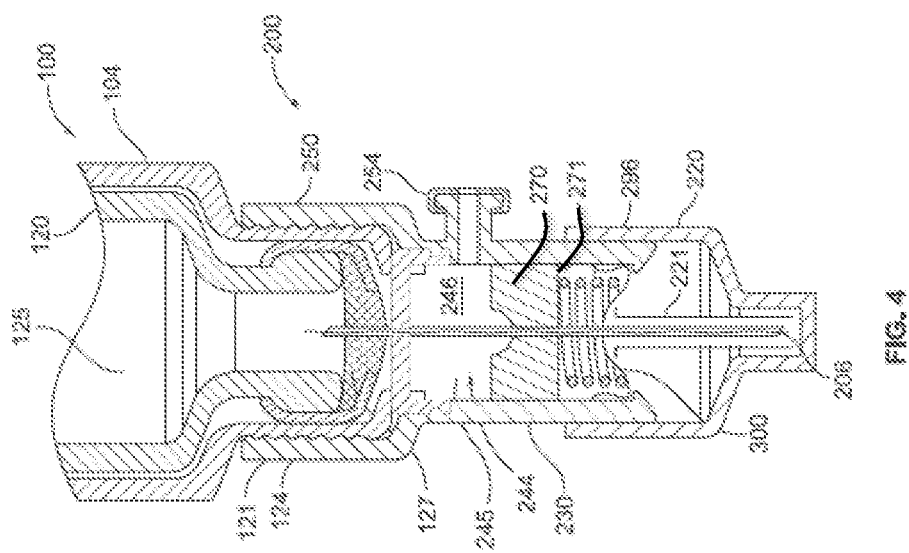

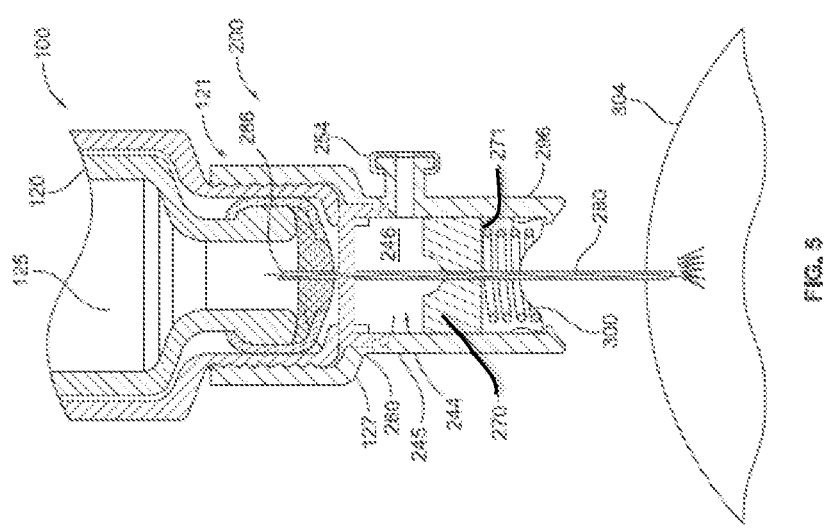

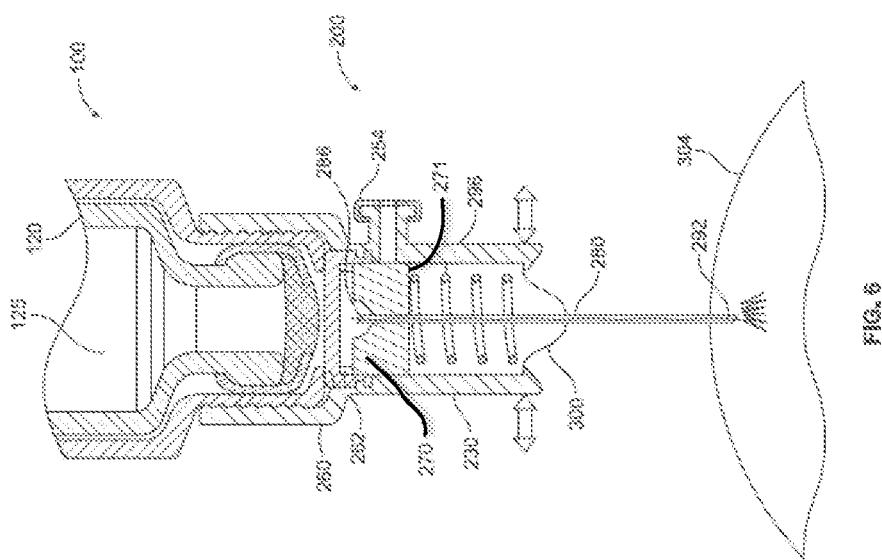

NEEDLE ASSEMBLY WITH RELEASE MECHANISM

CROSS REFERENCE TO RELATED APPLICATIONS

The present application is a U.S. National Phase Application pursuant to 35 U.S.C. §371 of International Application No. PCT/EP2011/066800 filed Sep. 28, 2011, which claims priority to U.S. Provisional Patent Application No. 61/388,644 filed Oct. 1, 2010 and European Patent Application No. 10190793.9 filed Nov. 11, 2010. The entire disclosure contents of these applications are herewith incorporated by reference into the present application.

FIELD OF DISCLOSURE

Specific embodiments of the present disclosure relate to medical devices and methods of delivering at least two drug agents from separate reservoirs using devices having only a single dose setting mechanism and a single dispense interface. A single delivery procedure initiated by the user may cause a fixed dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, the present disclosure concerns a needle assembly with a release mechanism that allows a second medicament contained within the needle assembly to be administered.

BACKGROUND

Certain disease states require treatment using one or more different medicaments. Some drug compounds need to be delivered in a specific relationship with each other in order to deliver the optimum therapeutic dose. The presently proposed assemblies, devices, and methods are of particular benefit where combination therapy is desirable, but not possible in a single formulation for reasons such as, but not limited to, stability, compromised therapeutic performance and toxicology.

For example, in some cases it might be beneficial to treat a diabetic with a long-acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it may be advantageous to store the active components separately and combine them at the point of delivery, e.g. injection, needle-less injection, pumps, or inhalation. However, the process for combining the two agents needs to be simple and convenient for the user to perform reliably, repeatedly and safely.

A further potential problem is that the quantities and/or proportions of each active agent making up the combination therapy may need to be varied for each user or at different stages of his therapy. For example, one or more active agents may require a titration period to gradually introduce a patient up to a "maintenance" dose. A further example would be if one active agent requires a non-adjustable fixed dose while the other is varied in response to a patient's symptoms or physical condition. This potential problem means that pre-mixed formulations of multiple active agents may not be suitable as these pre-mixed formulations would have a fixed ratio of the active components, which could not be varied by the healthcare professional or user.

Additional problems can arise where a multi-drug compound therapy is required, because certain users may not be able to cope with having to use more that one drug delivery system or to make the necessary accurate calculation of the required dose combination. This is especially true for users with dexterity or computational difficulties.

Accordingly, there exists a need to provide assemblies, devices, and methods for the delivery of two or more medicaments in a single injection or delivery step that is simple for the user to perform. The presently proposed assemblies, devices, and methods overcome the above-mentioned problems by providing separate storage containers or reservoirs for two or more active drug agents (e.g. a first or primary medicament and a second or secondary medicament).

Specifically, a needle assembly is attachable to a drug delivery device containing a first medicament. The needle assembly may comprise a main body and a septum positioned within a cavity defined in part by the main body. A stopper may be positioned within the cavity such that the main body cavity, the septum, and the stopper define a reservoir. A needle having a proximal end may be positioned in the stopper and a release mechanism may be positioned near a distal end of the main body. A biasing element may be positioned to drive the stopper such that, during a dose dispensing step of the drug delivery device, the release mechanism may be activated to drive the proximal end of the needle out of the septum so that the proximal end of the needle resides in the reservoir. The biasing element may also drive the stopper proximally. A second medicament may be provided in the reservoir of the needle assembly. In addition, this reservoir of the needle assembly may be filled with the second medicament by way of a sealable opening. This sealable opening may be provided on the main body.

The proposed assemblies, devices, and methods may also give the opportunity for varying the quantity of one or both the first and second medicaments. For example, one fluid quantity can be varied by changing the properties of the needle assemblies and/or injection device (e.g. dialing a user variable dose and/or changing the device's "fixed" dose). The second fluid quantity can be changed by manufacturing a variety of secondary drug containing packages with each variant comprising a reservoir containing a different volume and/or concentration of the second active agent. The user or healthcare professional would then be able to select the most appropriate secondary package or series or combination of series of different packages for a particular treatment regime. In an other example, the quantity of the second medicament delivered during dispense may be varied by varying the user variable dose of the first medicament.

These and other advantages will become evident from the following more detailed description of the invention.

One of the problems to be solved by the present invention is to provide a needle assembly and a method where the safety and the comfort of the user is increased.

SUMMARY

The disclosed assemblies, devices, and methods may allow for complex combinations of multiple drug compounds within a single drug delivery system. The disclosed assemblies, devices, and methods may allow the user to set and dispense a multi-drug compound device through one single dose setting mechanism and a single dispense interface. This single dose setter may control the mechanism of the device such that a combination of the individual drug compounds may be delivered when a single dose of one of the medicaments is set and dispensed through the single dispense interface. Further, the assemblies of the drug delivery system disclosed herein may include a second medicament contained within a main body reservoir defined by the assembly.

By defining the therapeutic relationship between the individual drug compounds, the disclosed delivery devices, assemblies, and delivery methods help ensure that a patient/user receives the optimum therapeutic combination dose from a multi-drug compound device without the inherent risks associated with multiple inputs where the user has to calculate and set the correct dose combination every time he uses the device. In given examples, the medicaments can be fluids, defined herein as liquids or gases or powders that are capable of flowing and that change shape at a steady rate when acted upon by a force tending to change its shape.

The disclosed concepts may be of particular benefit to users with dexterity or computational difficulties as the single input and associated predefined therapeutic profile can remove the need for them to calculate a prescribed dose every time they use the device and the single input allows considerably easier setting and dispensing of the combined compounds.

In a preferred embodiment, a master drug compound or a first medicament, such as insulin, contained within a multiple dose, user selectable device could be used with a single use, user replaceable, needle assembly that can contain a single dose of a second medicament and the single dispense interface. When connected to the primary device, the second compound may be activated/delivered after the dispense of the first compound. Although the present application specifically mentions insulin, insulin analogs or insulin derivatives, and GLP-1 or GLP-1 analogues as two possible drug combinations, other drugs or drug combinations, such as an analgesics, hormones, beta agonists or corticosteroids, or a combination of any of the above-mentioned drugs could be used with our disclosed systems and methods.

For the purposes of the present disclosure the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ωcarboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

According to one embodiment, a needle assembly is provided. The needle assembly may be, preferably releasably, attachable to a drug delivery device. The drug delivery device may contain a, preferably primary, medicament, preferably a plurality of doses of the primary medicament. The needle assembly may comprise a main body. The main body may be configured for attachment to the drug delivery device. The main body may define a cavity. A septum may be positioned within this main body, in particular within the cavity of the main body. A stopper may be positioned within the main body, in particular within the cavity of the main body. The stopper and the septum may be positioned such that the main body cavity, the septum, and the stopper define a reservoir. The reservoir may be configured for holding a, preferably second, medicament, preferably a single dose of the second medicament. The second medicament may be equal to the primary medicament or may be a different medicament. The needle assembly may comprise a needle. The needle may have a proximal end. The needle may have a distal end. The needle may be a double ended needle. The needle may be positioned in the stopper. The needle may be positioned in the septum. The needle assembly may comprise a release mechanism. The release mechanism may be positioned in the main body, in particular near a distal end of the main body. The needle assembly may comprise a biasing element. The biasing element may be positioned in the main body. The biasing element may be positioned to drive the stopper such that, during a dose dispensing step, the release mechanism may be activated. The release mechanism may be activated to drive the needle, in particular the proximal end of the needle, out of the septum so that the proximal end of the needle may reside in the reservoir. The biasing element may drive the stopper proximally. The second medicament may be provided in the reservoir of the needle assembly. Due to proximal movement of the stopper, the second medicament may be driven out of the reservoir via the needle. The needle assembly, in particular the main body, may comprise a sealable opening. The needle assembly may be filled with the second medicament by way of the sealable opening. In particular, the second medicament may be placed into said reservoir by way of said sealable opening. The sealable opening may be provided on the main body.

According to an embodiment, said second or secondary medicament comprises a GLP-1 or GLP-1 analog. Alternatively, said second medicament may comprise a premix of insulin and a GLP-1.

According to an embodiment, the needle assembly further comprises a needle cap. The needle cap may be a needle guard. Said needle cap may be, preferably removably, secured to the needle assembly, in particular to a distal end of said needle assembly. The needle cap may be secured so as to cover the distal end of said double ended needle. The needle cap may be configured for protecting the needle, in particular the distal end of the needle, against environmental influences. Furthermore, the needle cap may be adapted and arranged to prevent a user from needlestick injuries.

According to an embodiment, the needle assembly further comprises a protective seal. Said seal may be provided to cover a proximal end of said main body of said needle assembly.

According to an embodiment, said biasing element comprises a compression spring. Additionally or alternatively, said biasing element may comprise a cylindrical spring. Alternatively, said biasing element may comprise a disk spring. Alternatively, said biasing element may comprise a gas pressure spring.

According to one aspect, a needle assembly is provided that may be attachable to a drug delivery device. In one embodiment the needle assembly may be releasably attachable to a drug delivery device. The drug delivery device may comprise a drug reservoir. The drug reservoir may comprise a cartridge. The drug reservoir may hold a first medicament, preferably a plurality of doses of the first medicament. The drug delivery device, in particular the primary reservoir, can be filled with a first medicament before the needle assembly is attached to the device. The needle assembly may be particularly suited for an injection device, for example a pen type injection device. The drug delivery device may be suitable to set and dispense a dose of the first medicament held in the primary reservoir before the needle assembly is attached to the device or after the needle assembly was removed from the device. Accordingly, the device may be suitable to form a stand-alone device, configured to operate also in absence of the needle assembly according to the present disclosure, for example. For this purpose, a needle cannula may be, preferably removably, attachable to the distal end of the drug delivery device.

The drug delivery device may comprise a dose button. The dose button can be any triggering mechanism that causes a dose of the first medicament to be dispensed from the device. The dose button may be a dose dial button.

According to an embodiment, said release mechanism of said needle assembly comprises a catch spring. The catch spring may comprise spring properties.

The release mechanism may be adapted and arranged to pull the needle out of the septum of the needle assembly. In addition, the release mechanism may be configured to pull the needle out of a septum of the drug reservoir of the drug delivery device.

The catch spring of the release mechanism may comprise a first state, in particular a first stable state. The catch spring may comprise a second state, in particular a second stable state. The catch spring may be switchable from the first state into the second state. When the catch spring switches from the first state into the second state, the release mechanism may trigger removal of the needle out of the previously mentioned septum of the needle assembly. The catch spring may be configured to mechanically cooperate with the biasing element. In particular, in the first state, the catch spring may be configured to keep the biasing element in a compressed condition. The biasing element may be allowed to decompress when the catch spring was switched from the first state into the second state.

According to an embodiment the release mechanism may be triggered by the dose setter of a drug delivery device, wherein the dose setter and the release element are mechanically coupled so that the release element is triggered end of dispense of the primary medicament.

According to an embodiment the release mechanism may be configured to be operably connected to the drug delivery device. The operable connection may be releasable.

According to an embodiment the release mechanism may be configured to be operably connected to the drug delivery device. The connection may be arranged to switch the state of the catch spring from a first state to a second state.

According to an embodiment the release mechanism may be configured to be operably connected to the drug delivery device. The connection may be arranged to switch the state of the catch spring. In particular, the connection may be arranged to switch the state of the catch spring at the end of dispense of the medicament from the drug delivery device. The operable connection may comprise at least one coupling element that operably connects a dose button of the drug delivery device to the catch spring. Preferably the connection is established when the dose button is in its distal or "zero" position.

According to an embodiment the connection may comprise at least one detecting element arranged to detect dispense of medicament from the drug delivery device. The detecting element could detect movement of a piston inside a cartridge of the drug delivery device. Alternatively, the detecting element could detect movement of a plunger moving the piston or movement of another element that is correlated with dispense of the medicament. Alternatively, the detecting element could detect flow of medicament. The detecting element could be mechanical, electrical, optical, or a combination thereof.

According to an embodiment the detecting element detects dispense of medicament from the drug delivery device and the coupling element establishes connection between the dose button and the switch element when the dose button is in its distal or "zero" position. The combination of these features provides for ensuring that (a) the first medicament form the drug delivery device has been dispensed and (b) that the dispense is at its end. This prevents the release mechanism of the needle assembly from being triggered without intention. For example, a user might correct a dose in reducing the set amount of medicament. The amount may be reduced even that the dose button is in its "zero" position. However, the release mechanism will not be triggered because the detecting element did not detect dispense of the first medicament from the drug delivery device.

According to an embodiment, said main body is configured for, preferably releasable, attachment to said drug delivery device. The main body may be attachable to the device by way of a connection mechanism. The connection mechanism may comprise a thread, for example.

A further aspect relates to a method of dispensing a, for example first, medicament from a needle assembly is disclosed. The method may be used for test purposes. In particular, the method may be applicable for non-therapeutic and/or non-surgical purposes. The needle assembly may be, preferably releasably, attachable to a drug delivery device. The needle assembly may comprise the previously described needle assembly, for example. The method may comprise the step of providing a main body of the needle assembly. The method may comprise the step of configuring the main body for, preferably releasable, attachment to the drug delivery device. The method may comprise the step of positioning a septum within a cavity of the main body. The method may further include the step of positioning a stopper within the cavity. The stopper may be positioned such that the main body cavity, the septum, and the stopper may define a reservoir for a second medicament. The method may further include the step of positioning a needle in the stopper. The method may further include the step of positioning the needle in the septum. The needle may have a distal end. The needle may have a proximal end. The method may further include the step of positioning a release mechanism near a distal end of the main body. The release mechanism may comprise a catch spring. The method may further include the step of providing a biasing element. The biasing element may be configured to drive the stopper. In particular, the biasing element may be biased to drive the stopper. The method may further include the step of initiating a dose dispensing step of the drug delivery device, e.g. by means of a dose setting mechanism of the device. The method may further include the step of activating the release mechanism to drive the proximal end of the needle out of the septum so that the proximal end may reside in the reservoir. The method may further include the step of utilizing the biasing element, e.g. a compression spring, to drive the stopper proximally. The method may also include the step of providing the second medicament, in particular of filling the reservoir with the second medicament. The method may also include the step of providing a sealable opening on said main body. In one preferred arrangement, the step of filling the reservoir with the second medicament may take place by way of the sealable opening.

Certain needle assemblies in accordance with the present disclosure can be designed for use with a drug delivery device with an appropriate compatible interface. However, it may be preferable to design the needle assembly or needle module in such a way as to limit its use to one exclusive primary drug delivery device (or family of devices) through employment of dedicated or coded features to prevent attachment of a non-appropriate needle assembly to a non-matching device. In some situations, it may be beneficial to ensure that the needle assembly is exclusive to one drug delivery device while also permitting the attachment of a standard drug dispense interface to the device. This would allow the user to deliver a combined therapy when the needle assembly is attached, but would also allow delivery of the first medicament or primary compound independently through a standard drug dispense interface in situations, such as, but not limited to, dose splitting or top-up of the primary compound.

In an embodiment, the primary drug delivery device is used more than once and, therefore, is a multi-use device. However, the drug delivery device may also be a single use disposable device. Such a device may or may not have a replaceable reservoir of the primary drug compound, but the proposed concepts are equally applicable to both scenarios. It is also possible to have a suite of different needle assemblies for various conditions that could be prescribed as one-off extra medication to patients already using a standard drug delivery device.

A further proposed feature is that both medicaments are delivered via one injection needle and during one injection of the injection site. This may offer a convenient benefit to the user in terms of reduced user steps compared to administering two separate injections. This convenience benefit may also result in improved compliance with the prescribed therapy, particularly for users who find injections unpleasant or who have computational or dexterity difficulties.

According to a preferred embodiment, a needle assembly attachable to a drug delivery device is provided, the needle assembly comprising:

a main body, said main body defining a medicament cavity;
a septum positioned within said cavity of said main body;
a stopper positioned within said cavity such that said main body cavity, said septum and said stopper define a reservoir;
a double ended needle positioned in said stopper and said septum, said double ended needle comprising a proximal end and a distal end;
a release mechanism; and
a biasing element positioned to drive said stopper.

Said release mechanism is configured to drive said proximal end of said needle out of said septum so that said proximal end resides in said reservoir, and said biasing element is configured to drive said stopper proximally.

According to a preferred embodiment, a needle assembly attachable to a drug delivery device is containing a primary medicament is provided, the needle assembly comprising:

a main body configured for attachment to a drug delivery device, said body defining a medicament cavity;
a septum positioned within said cavity of said main body;
a stopper positioned within said cavity such that said main body cavity, said septum, and said stopper define a reservoir;
a double ended needle positioned in said stopper and said septum, said double ended needle comprising a proximal end and a distal end;
a release mechanism positioned near a distal end of said main body; and
a biasing element positioned to drive said stopper;

During a dose dispensing step, said release mechanism drives said proximal end of said needle out of said septum so that said proximal end resides in said reservoir, and said biasing element drives said stopper proximally.

According to a preferred embodiment, a method of dispensing a medicament from a needle assembly attachable to a drug delivery device is provided, the method comprising the steps of:

configuring a needle assembly main body for attachment to the drug delivery device;
positioning a septum within a cavity of said main body;
positioning a stopper within said cavity such that said main body cavity, said septum and said stopper define a reservoir for the medicament;
positioning a needle in said septum;
positioning a release mechanism element near a distal end of said main body;
biasing an element to drive said stopper;
initiating a dose dispensing step of said drug delivery device;
activating said release mechanism element to drive a proximal end of said needle out of said septum so that said proximal end resides in said reservoir of the needle assembly, and
utilizing said element to drive said stopper proximally.

According to a preferred embodiment, a method of dispensing a first medicament from a needle assembly attachable to a drug delivery device is provided, the method comprising the steps of:

configuring a needle assembly main body for attachment to a drug delivery device;
positioning a septum within a cavity of said main body;
positioning a stopper within said cavity such that said main body cavity, said septum, and said stopper define a reservoir for a first medicament;
positioning a needle having a proximal end in said stopper;
positioning a release mechanism catch spring near a distal end of said main body; and
biasing a element to drive said stopper;

initiating a dose dispensing step of said drug delivery device;

activating said catch spring to drive said proximal end of said needle out of said septum so that said proximal end resides in said reservoir, and utilizing said compression spring to drive said stopper proximally.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 4 illustrates a cross-sectional view of the exemplary needle assembly illustrated in FIG. 3 attached to an exemplary drug delivery device, such as the drug delivery device illustrated in FIG. 1;

FIG. 5 illustrates a cross-sectional view of the exemplary needle assembly illustrated in FIG. 3 attached to an exemplary drug delivery device during a first injection step; and FIG. 6 illustrates a cross-sectional view of the exemplary needle assembly illustrated in FIG. 3 during a second injection step.

DETAILED DESCRIPTION

The present disclosure provides for a system and method for delivering a dose of a first medicament and a second medicament via a single dispense interface, where such a single dispense interface may comprise a double ended needle. The present disclosure specifically relates to a needle assembly that comprises a reservoir that can hold at least one fixed dose of the second medicament, such as a GLP-1 or GLP-1 analog.

Figure 1:
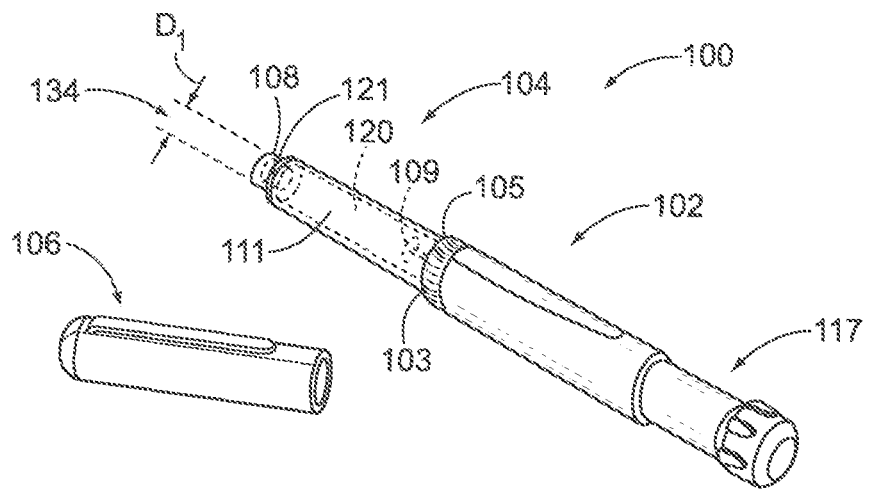
FIG. 1 illustrates an exemplary drug delivery device.

A needle assembly in accordance with embodiments of the present disclosure may be attached to a drug delivery device containing a medicament, such as drug delivery device 100. The second medicament may be equal to the medicament contained in the device 100. Alternatively, the second medicament may be different to the medicament contained in the device 100. For example, FIG. 1 illustrates the drug delivery device 100 in the form of a pen type drug delivery device. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The pen type drug delivery device 100 may comprise a re-usable or a disposable pen type syringe. Where the syringe comprises a reusable device, the cartridge holder 104 and the dose setting mechanism 102 are removably coupled together. In a disposable device, they are permanently coupled together. In FIG. 1, the dose setting mechanism 102 comprises a piston rod 109, such as a threaded piston rod that rotates when a dose is injected.

To inject a previously set dose, a double ended needle assembly (not explicitly shown) may be attached to a distal end 108 of the cartridge holder 104. Preferably, the distal end 108 of the holder 104 comprises a thread 121 (or other suitable connecting mechanism such as a snap lock, snap fit, form fit, or bayonet lock mechanism) so that the needle assembly may be removably attached to the distal end 108 of the holder 104. When the drug delivery device 100 is not in use, the removable cap 106 can be releasably retained over the cartridge holder 104.

Figure 2:
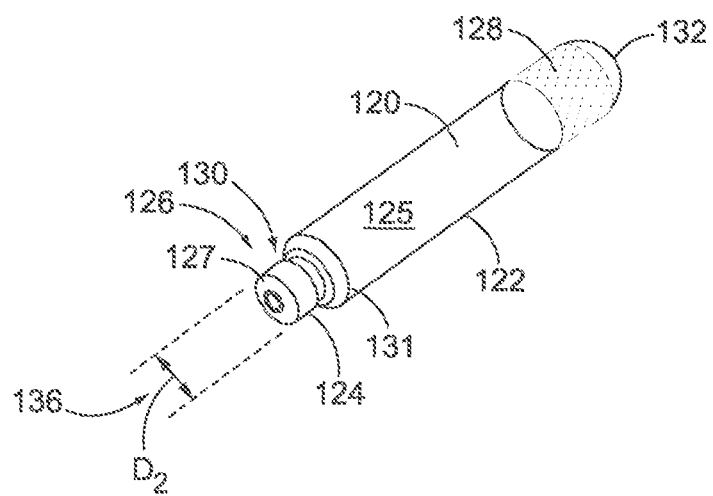
FIG. 2 illustrates an exemplary drug cartridge for use with a drug delivery device, such as the drug delivery device illustrated in FIG. 1.

An inner cartridge cavity 111 defined by the cartridge holder 104 is dimensioned and configured to securely receive and retain a cartridge 120. FIG. 2 illustrates a perspective view of the cartridge 120 that may be used with the drug delivery device 100 illustrated in FIG. 1. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck 126 projects distally from the shoulder 131 of the barrel 122. Preferably, this smaller diameter neck 126 is provided with a large diameter annular bead and this bead extends circumferentially thereabout at the extreme distal end of the neck 126. A pierceable seal or septum 127 is securely mounted across the open distal end 130 defined by the neck 126. The seal 127 may be held in place by a metallic sleeve or ferrule 124. This ferrule 124 may be crimped around the circumferential bead at the distal end of the neck 126. A medicament 125 is pre-filled into the cartridge 120 and is retained within the cartridge 120, in part, by the pierceable seal 127, the metallic sleeve 124, and a stopper 128. The stopper 128 is in sliding fluid-tight engagement with the inner tubular wall of the barrel 122. Axially directed forces acting upon the stopper 128 during dose injection or dose administration urges the medication 125 from the cartridge 120 though a double ended needle mounted onto the distal end 130 of the cartridge holder 104 and into the injection site. Such axial forces may be provided by the piston rod 109.

Returning to FIG. 1, a portion of the cartridge holder 104 defining the cartridge holder cavity 111 is of substantially uniform diameter represented in FIG. 1 by D1 134. This diameter D1 134 is preferably slightly greater than the diameter D2 136 of the cartridge 120 (see FIG. 2). The interior of the cartridge holder 104 includes an inwardly-extending annual portion or stop that is dimensioned to prevent the cartridge 120 from moving within the cartridge holder 104. In this manner, when the cartridge 120 is loaded into the cavity 111 of the cartridge holder 104 and the cartridge holder 104 is then connected to the dose setting mechanism 102, the cartridge 120 will be securely held within the cartridge cavity 111. More particularly, the neck 126 and ferrule 124 of the cartridge 120 are inserted in a proximal to distal direction into the open proximal end 105 of the cartridge holder 104 with the ferrule 124 eventually passing entirely into the holder 104. With the holder 104 removably coupled to the dose setting mechanism 102, the proximal end 132 of the cartridge 120 will typically abut a stop provided by the dose setting mechanism 102.

A number of doses of the medicament 125 may be dispensed from the cartridge 120. It will be understood that the cartridge 120 may contain a type of medicament 125 that must be administered often, such as one or more times a day. One such medicament 125 is insulin. The stopper or movable piston 128 is retained in the first end or proximal end 132 of the cartridge 120 and receives an axial force created by the piston rod 109 of the dose setting mechanism 102.

The dose setting mechanism 102 comprises a dose setter 117 at the proximal 107 end of the dose setting mechanism 102. In one preferred embodiment, the dose setter 117 may extend along the entire length of the dose setting mechanism 102. The dose setter 117 may be rotated by a user so as to set a dose.

To administer a dose that may be set by rotating the dose setter 117, the user attaches the needle assembly comprising a double ended needle on the distal end 108 of the cartridge holder 104. In this manner, a proximal extending needle of the needle assembly pierces the seal 127 of the cartridge 120 and is, therefore, in liquid communication with the medicament 125. The user pushes on the dose setter 117 to inject the set dose. The same dose setting and dose administration procedure is followed until the medicament 125 in the cartridge 120 is expended and, then, a new cartridge must be loaded in the device 100. To exchange an empty cartridge 120, the user is called upon to remove the cartridge holder 104 from the dose setting mechanism 102.

Figure 3:
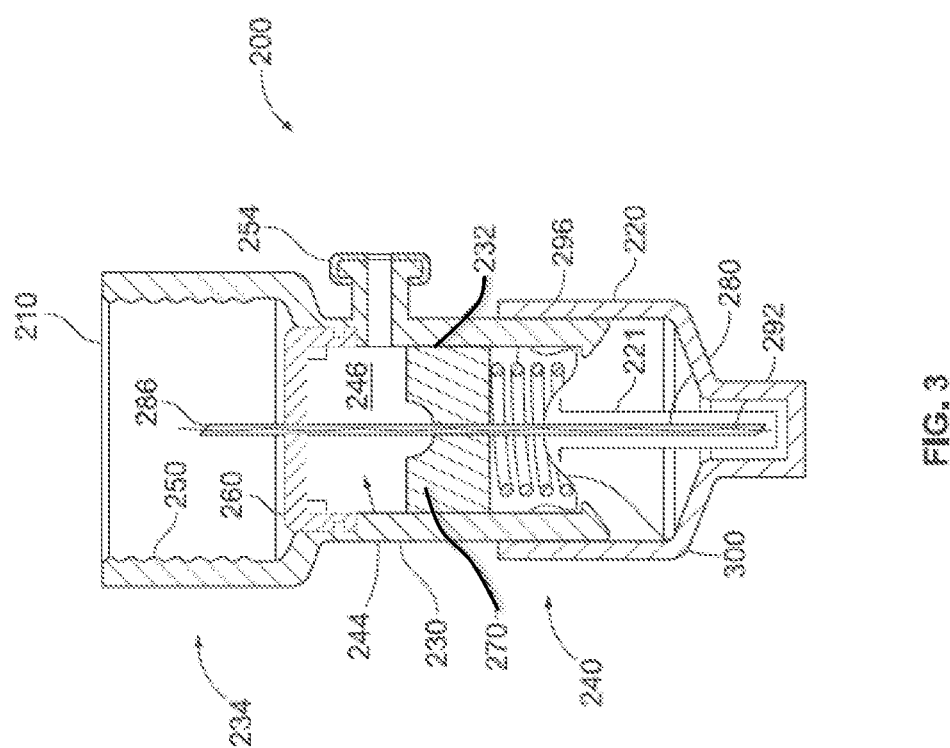
FIG. 3 illustrates a cross-sectional view of an exemplary needle assembly as provided to a user in a packaged condition.

FIG. 3 illustrates a cross-sectional view of an exemplary needle assembly 200 as provided to a user in a sterile condition. The needle assembly 200 is preferably self-contained and provided as a sealed and sterile disposable needle assembly that has an attachment means compatible to the thread 121 at the distal end 108 of the cartridge holder 104. The needle assembly 200 could be supplied by a manufacturer contained in a protective and sterile container, where the user would peel or rip open a seal or the container itself to gain access to the sterile needle assembly 200.

FIG. 3 illustrates the exemplary needle assembly 200. Such an exemplary needle assembly 200 may be configured for attachment to a drug delivery device containing a primary medicament 205, such as the device 100 illustrated in FIG. 1. In FIG. 3, the needle assembly 200 is illustrated in one arrangement where the assembly 200 is provided in a sterile state to the user.

To this end, the needle assembly 200 is illustrated as comprising a protective film 210 provided at a proximal end of the needle assembly 200. The needle assembly 200 further can comprise a needle cap 220 that may be provided at a distal end of the needle assembly 200. Before a user mounts the needle assembly 200 onto the distal end of the drug delivery device, such as drug delivery device 100, the protective film 210 may be removed so that the proximal end of the needle assembly 200 can be releasably attached to a drug delivery device, such as the drug delivery device 100.

As illustrated, the needle assembly 200 further comprises a main body 230 and this main body 230 extends from a main body proximal end 234 to a main body distal end 240. The protective film or seal 210 is provided at the proximal end 234 of this main body 230 and this protective seal 210 provides a sterile seal of the proximal end of the needle assembly 200. In one preferred arrangement, the needle cap 220 is provided at the distal end 240 of the main body 230. This needle cap 220 may be removably secured by way of a snap lock, snap fit, bayonet lock or other similar connection mechanism. A second needle cover or cap 221 may also be provided. Prior to injection, the user would remove both the first needle cover or cap 220 and the second needle cover or cap 221.

As illustrated in FIG. 4, the needle assembly 200 can be attached to the connection means or thread 121 of distal end of the drug delivery device 100, in particular of the cartridge holder 104, illustrated in FIG. 1. As illustrated, the proximal end 234 of the main body 230 of the needle assembly 200 may further comprise a connection mechanism 250. In one arrangement, this connection mechanism 250 may comprise at least a complete or a partial internal thread or groove. For example, such a thread or groove arrangement may be a single or double start thread or groove. In addition, such a groove or thread arrangement may be configured so as to allow the needle assembly 200 to be removably attached to the distal end of a drug delivery device, such as the distal end of the drug delivery device 100 illustrated in FIG. 1. Alternatively, this connection mechanism 250 may comprise other types of removable couplings generally known in the art such as, but not limited to, snap locks, snap fits, form fits, bayonet couplings or other similar type coupling mechanisms.

Referring now to both FIGS. 3 and 4, a pierceable septum 260 is provided within a cavity 244 defined by the main body 230. This septum 260 is located generally near the proximal end 234 of the main body 230. As will be described below, this septum 260 comprises a pierceable septum and can be pierced by a proximal end of a double ended needle. In one preferred arrangement, the pierceable septum 260 provides for a fluid tight seal for a medicament contained within the needle assembly 200.

The needle assembly 200 further comprises a moveable stopper 270. In one preferred arrangement, this moveable stopper 270 is in fluid tight engagement with an inner wall 232 of the main body 230. During an injection step, this stopper 270 can be moved from a first distal position to a second or a proximal position. For example, in FIGS. 3-5, the moveable stopper 270 is illustrated in a distal position or first position. In FIG. 6, the moveable stopper 270 is illustrated in a proximal position or second position.

A biasing element 296, such as a spring, is also provided within the distal end 240 of the main body 230. As illustrated in FIG. 2, this spring is shown in a compressed state and is positioned between a distal surface 271 of the moveable stopper 270 and a catch spring 300. In such a compressed state, the biasing element 296 can exert a force onto the stopper 270 in the proximal direction. However, as the reservoir 245 is completely filled with the second medicament 246, the biasing element 296 cannot drive the second medicament 246 out of the reservoir 245 as the force exerted by the biasing element 296 is compensated by means of the incompressible medicament 246, in particular of the incompressible fluid. The second medicament 246 may be driveable out of the reservoir 245 when the catch spring 300 was switched from a first stable state, as shown in FIGS. 3 to 5, into a second stable state, as shown in FIG. 6, thereby moving the needle 280 out of the septum 260 and into the reservoir 245. This is described later on in more detail.

The catch spring 300 is also provided within the needle assembly 200. Initially, when the needle assembly 200 is mounted onto the drug delivery device 100 and during a first drug delivery step, this catch spring 300 helps to keep the biasing element 296 in a compressed state. Accordingly, the catch spring 300 is in the first state (FIGS. 3 to 5). Once activated, the catch spring 300 switches from the first state into the second state. Once activated, the catch spring 300 releases the biasing element 296 so that this biasing element 296 drives or moves the moveable stopper 270 from the first or distal position towards a second or proximal position. In addition, as will be described in greater detail below, the catch spring 300 also assists in moving the double ended needle out of fluid engagement with the medicament 125 of the drug delivery device 100 and into fluid engagement with the medicament contained with the needle assembly 200.

The main body 230 further comprises at least one sealable opening 254. This sealable opening 254 may be used to fill a medicament 246 within the cavity 244 defined by the main body 230. In one arrangement, this sealable opening 254 is used to fill a fixed dose of the medicament 246 within the cavity of the main body 230. In another arrangement, this sealable opening 254 is used to fill a fixed dose of a GLP-1 or a GLP-1 analog within the cavity 244. After the medicament 246 has been filled within the cavity 244, the sealable opening 254 may be sealed, e.g. with a septum or stopper made of any elastomeric material or plastic material.

The needle assembly 200 further comprises a double ended needle 280 and this double ended needle 280 comprises a first or proximal piercing end 286 and a second or distal piercing end 292. As illustrated in FIG. 3, within the needle assembly 200, a proximal section of this double ended needle 280 resides within the septum 260 while a central section of this double ended needle 280 resides within the moveable stopper 270. As illustrated in FIG. 4, after the needle assembly 200 is releasably coupled to the drug delivery or injection device 100 (as well as during one initial injection step), the proximal end 286 of the double ended needle 280 resides in fluid communication with the first medicament 125 contained within the drug delivery device 100. And as will be discussed below, in a subsequent injection step, the proximal end 286 of the double ended needle 280 will be in fluid communication with the second medicament 246 that may be contained within a main body reservoir 245 that can be defined in part by the septum 260, the main body cavity 244, and the movable stopper 270 of the needle assembly 200.

As can also be seen from FIG. 3, the needle assembly 202 may also include the connection mechanism or attachment means 250. The attachment means 250 may be configured to attach to a corresponding attachment means of drug delivery device 100, such as the attachment means or thread 121 at the distal end 108 of device 100, in particular of cartridge holder 104. Attachment means 250 is depicted as comprising a thread. However, this is intended as an example only and other attachment means are possible.

Further, in an exemplary embodiment, the needle assembly 200 may also comprise the first needle cap or needle guard 220. The needle cap 220 may have a connection feature (e.g. a snap-fit feature) that can allow the cover to be removably attached to an outer surface of the main body 230 of the needle assembly 200. In one arrangement, the needle cover or needle guard 220 may substantially conceal the needle distal end 206 of the double ended needle 280 from a user's view so as to beneficially reduce any needle anxiety that a patient may be experiencing. While substantially concealing the needle, the needle cover or cap 220 also helps to prevent inadvertent needle sticks.

In order to use the needle assembly 200 to inject a dose of the first medicament 125 from the drug delivery device 100 and the second medicament 246 contained within the needle assembly reservoir 245, the user will remove the protective film 210 at the proximal end of the needle assembly 200, and mount the needle assembly 200 to the drug delivery device 100. For example, FIG. 4 illustrates a cross-sectional view of the exemplary needle assembly 200 illustrated in FIG. 3 attached to the exemplary drug delivery device 100, such as the device illustrated in FIG. 1. Only the distal end of the drug delivery device 100 is illustrated in FIG. 4. As illustrated, this drug delivery device 100 comprises the cartridge holder 104 comprising the thread or connection mechanism 121 at the distal end 108 of the cartridge holder 104. This connection mechanism 121 is configured to releasably engage the connection mechanism 250 of the needle assembly 200. As illustrated, the cartridge holder 104 further comprises a reservoir (e.g. the cartridge) 120 containing the primary medicament 125, where such medicament comprises a insulin. As is typical in the drug delivery device art, the illustrated reservoir or cartridge 120 comprises a septum 127 and a ferrule 124, similar to the cartridge illustrated in FIG. 2.

As illustrated in FIG. 4, attachment of the needle assembly 200 to drug delivery device 100 causes the proximal end 286 of the double ended needle 280 to penetrate the septum 127 of the cartridge 120 in the drug delivery device 100. When this proximal end 286 of the double ended needle 280 has passed through the septum 127, fluid communication is established between the primary medicament 125 contained within the cartridge 120 and the double ended needle 280. After the needle assembly 200 was attached to the drug delivery device 100 as illustrated in FIG. 4, a user may set a user-settable dose of the first medicament 125. The dose of the drug delivery device 100 may be set in a usual manner (e.g. by dialling out an appropriate number of units of the primary medicament with dose dial or dose setter 117 of drug delivery device 100) as described above with reference to FIG. 1.

FIG. 5 illustrates a cross-sectional view of the exemplary needle assembly 200 illustrated in FIGS. 3 and 4 attached to the exemplary drug delivery device 100 during a first injection step where the first medicament 125 is dispensed. Dispense of the first medicament 125 contained with the cartridge 120 may be achieved via activation of the dosing mechanism 102 of the drug delivery device 100. During this initial injection step, a dose of the medicament 125 contained within the drug delivery device 100 is administrated to an injection site 304 by way of the double ended needle 280.

Specifically, during dispense, as a user depresses the dose setter 117 of the drug delivery device 100, the first medicament 125 is forced in distal direction toward the double ended needle 280 and into the injection site 304 (such as a patient's injection site). As the first medicament 125 is dispensed from the cartridge 120 of drug delivery device 100, the first medicament 125 flows through the double ended needle 280.

At the end of this initial injection step of the first medicament 125, a switching or release mechanism may be triggered that switches the open end of the proximal end 286 of double ended needle 280 from medicament 125 to medicament 246. The release mechanism may comprise the catch spring 300. The catch spring 300 may be connected to a dose setter 117 of the drug delivery device (not shown). The dose setter 117 may trigger the catch spring 300 contained within the needle assembly 200. In particular, a distal movement of the dose setter 117 may trigger switching of the catch spring 300 from the first state into the second state. This catch spring 300 can be made of metal or plastic materials or combinations thereof. The catch spring 300 should feature typical spring properties and designs as used for other medical or technical devices. The catch spring 300 acts to pull the double ended needle 280 out of the septum 127 of the cartridge 120. In addition, the catch spring 300 also acts to pull the double ended needle 280 out of the septum 260 of the needle assembly 200. As such, the proximal end 286 of double ended needle 280 is withdrawn from being in fluid communication with the medicament 125 contained within the cartridge 120. In place of the catch spring 300, other mechanisms are also conceivable that pull the needle into this second or distal position. Such mechanisms can include kinematic, hydraulic, pneumatic, magnetic, electro-magnetic, or osmotic driven mechanisms. It is vital that the respective mechanism is coupled to the dose setting or dosing mechanism 102.

FIG. 6 illustrates a cross-sectional view of the exemplary needle assembly 200 illustrated in FIG. 3 during a second injection step. During this second injection step, injection of the medicament 246 contained within the reservoir 245 of the needle assembly 200 may take place. This subsequent injection step may take place when driven by the biasing element 296. The biasing element 296 may comprise a metal spring, a disk spring, a cylindrical compression spring, or a conical spring, a plastic element, or a gas pressure spring. Preferably, once activated, this biasing element 296 drives the moveable stopper 270 in a proximal direction and this stopper 270 moves along a predetermined path a known distance. Thereby, the second medicament 246 flows through the needle 280 and out of the needle assembly 200. The moveable stopper 270 moves in the proximal direction until it resides in a second or proximal position defined in part by a stop 262 provided by the septum 260. This stop 262 may be located along a distal surface of the septum 260 of the needle assembly 200. In one preferred arrangement, it is this known distance that the stopper 270 moves that determines the amount of the second medicament 246 that is injected during this subsequent injection step. By adjusting the amount of stopper movement (e.g. by varying where the stop 262 is located), the amount of second medicament 246 injected during this second injection step can be varied.

After the user finished dispensing of the first medicament 125 and the second medicament 246, the user may remove the distal end 292 of the double ended needle 280 from the injection site 304. Then, the needle assembly 200 no longer containing the second medicament 246 may be disposed of. Assuming that the drug delivery device 100 still contains at least one dose first medicament 125, the drug delivery device 100 may be reused by the patient as required.

The steps of setting and/or dispensing a dose may be applicable for non-therapeutic and/or non-surgical purposes. In particular, said steps may be performed for test purposes, e.g. for testing the functionality of the device 100.

A needle assembly in accordance with the present disclosure may also include features to encourage or ensure single-use of the needle assembly 200. Such features may include a lock-out feature (not explicitly shown) that locks out the needle or a feature that prevents reattachment to another drug delivery device. Alternatively, features may be present that discourage subsequent dosing through the needle assembly via other means.

A needle assembly in accordance with the present disclosure offers numerous advantages. For example, the needle assembly allows a user to deliver a mixture of two medicaments, where the medicaments are combined upon attachment of a needle assembly to a drug delivery device. The needle assembly may allow a user to follow a variety of different therapeutic profiles, and the amount of the secondary medicament may be configured to meet a desired therapeutic profile.

The connection or attachment between the needle assembly of the herein described embodiments may contain additional features (not shown), such as connectors, stops, splines, ribs, grooves, and the like design features, that ensure that specific needle assembly are attachable only to matching drug delivery devices. Such additional features would help preventing the insertion of a non-appropriate needle assembly to a non-matching injection device.

The shape of the needle assembly may be a cylindrical body or any other geometric shape suitable for defining a fluid reservoir or for containing discrete self-contained reservoir of the medicament in the needle assembly and for attaching one or more needle cannulae. The integrated output needle can be any needle cannula suitable for subcutaneous or intramuscular injection. Preferably, the needle assembly is provided by a drug manufacturer as a stand-alone and separate device that is sealed to preserve sterility. The sterile seal of the needle assembly is preferably designed to be opened automatically, e.g. by cutting, tearing or peeling, when the needle assembly is advanced or attached to the drug delivery device by the user.

The needle assembly of the present disclosure should be designed to operate in conjunction with a multiple use injection device, preferably a pen-type multi-dose injection device similar to what is illustrated in FIG. 1. The injection device could be a reusable or disposable device. By disposable device it is meant an injection device that is obtained from the manufacturer preloaded with medicament and that cannot be reloaded with new medicament after the initial medicament is exhausted. The device may be a fixed dose or a settable dose and preferably a multi-dose device. However, in some cases, it may be beneficial to use a single dose, disposable device.

A typical injection device contains a cartridge or other reservoir of medication. This cartridge is typically cylindrical in shape and is usually manufactured in glass. The cartridge is sealed at one end with a rubber bung and at the other end by a rubber septum. The injection pen is designed to deliver multiple injections. The delivery mechanism is typically powered by a manual action of the user. However, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

The scope of the invention is defined by the content of the claims. The invention is not limited to specific embodiments but comprises any combination of elements of different embodiments. Moreover, the invention comprises any combination of claims and any combination of features disclosed by the claims.

The invention claimed is:

1. A needle assembly attachable to a drug delivery device, the needle assembly comprising:
   a main body, said main body defining a medicament cavity;
   a septum positioned within said cavity of said main body;
   a stopper positioned within said cavity such that said main body cavity, said septum and said stopper define a reservoir;
   a double ended needle positioned in said stopper and said septum, said double ended needle comprising a proximal end and a distal end;
   a release mechanism; and
   a biasing element positioned to drive said stopper;
   wherein, said release mechanism is configured to drive said proximal end of said needle out of said septum so that said proximal end resides in said reservoir, and said biasing element is configured to drive said stopper proximally.

2. The needle assembly of claim 1, further comprising a medicament contained within said reservoir of said needle assembly.

3. The needle assembly of claim 2, wherein said main body comprises a sealable opening and wherein the medicament is placeable into said reservoir by way of said sealable opening.

4. The needle assembly of claim 2, wherein said medicament comprises a GLP-1, a GLP-1 analog or a premix of insulin and a GLP.

5. The needle assembly according to claim 1, further comprising a needle cap, said needle cap being removably secured to a distal end of said needle assembly so as to cover the distal end of said double ended needle.

6. The needle assembly according to claim 1, further comprising a protective seal, said seal being provided to cover a proximal end of said main body of said needle assembly.

7. The needle assembly according to claim 1, wherein said biasing element comprises one of a compression spring, a disk spring and a gas pressure spring.

8. The needle assembly according to claim 1, wherein said drug delivery device comprises a drug reservoir holding a further medicament.

9. The needle assembly according to claim 1, wherein said release mechanism is positioned near a distal end of said main body, and wherein the release mechanism comprises a catch spring.

10. The needle assembly according to claim 1, wherein said main body is configured for attachment to said drug delivery device by way of a connection mechanism.

11. The needle assembly of claim 10, wherein said connection mechanism comprises a thread.

12. A method of dispensing a medicament from a needle assembly attachable to a drug delivery device, the method comprising the steps of:

configuring a needle assembly main body for attachment to the drug delivery device;

positioning a septum within a cavity of said main body;

positioning a stopper within said cavity such that said main body cavity, said septum and said stopper define a reservoir for the medicament;

positioning a needle in said septum;

positioning a release mechanism element near a distal end of said main body;

biasing an element to drive said stopper;

initiating a dose dispensing step of said drug delivery device;

activating said release mechanism element to drive a proximal end of said needle out of said septum so that said proximal end resides in said reservoir of the needle assembly, and utilizing said element to drive said stopper proximally.

13. The method of claim 12, further comprising the step of providing a sealable opening on said main body.

14. The method of claim 13, further comprising the step of providing the medicament into said reservoir by way of said sealable opening prior to driving the stopper proximally.

* * * * *